(12) United States Patent
Ruddle et al.

(10) Patent No.: US 7,549,861 B2
(45) Date of Patent: Jun. 23, 2009

(54) SYRINGE FOR A COMBINED DENTAL IRRIGATOR AND VACUUM DEVICE

(75) Inventors: Clifford J. Ruddle, 227 Las Alturas Rd., Santa Barbara, CA (US) 93103; Stephen Barker, Santa Barbara, CA (US)

(73) Assignee: Clifford J. Ruddle, Santa Clara, CA (US)

( * ) Notice: Subject to any disclaimer, the term of this patent is extended or adjusted under 35 U.S.C. 154(b) by 90 days.

(21) Appl. No.: 11/618,191

(22) Filed: Dec. 29, 2006

(65) Prior Publication Data

US 2008/0160479 A1    Jul. 3, 2008

(51) Int. Cl.
  *A61C 5/02* (2006.01)
  *A61G 5/02* (2006.01)
  *F04B 39/10* (2006.01)
  *B05B 11/02* (2006.01)

(52) U.S. Cl. .......................... 433/81; 433/80; 433/224; 222/631; 222/633; 222/209; 417/472; 417/571

(58) Field of Classification Search ................... 433/80, 433/81–82, 89, 224; 604/38, 19, 30, 35, 604/33, 68, 93.01, 118, 121, 131, 134, 135, 604/153, 181, 187, 185, 191, 235; 601/163–165; 222/631–633, 206, 209; 417/472, 571
See application file for complete search history.

(56) References Cited

U.S. PATENT DOCUMENTS

| 3,164,153 | A |   | 1/1965 | Carlo |        |
|-----------|---|---|--------|-------|--------|
| 3,398,743 | A | * | 8/1968 | Shalit | 604/36 |
| 3,745,655 | A |   | 7/1973 | Malmin |        |
| 3,816,921 | A |   | 6/1974 | Malmin |        |
| 3,818,907 | A | * | 6/1974 | Walton | 604/38 |
| 4,842,581 | A | * | 6/1989 | Davis  | 604/38 |

(Continued)

FOREIGN PATENT DOCUMENTS

FR    2588469 A    4/1987

OTHER PUBLICATIONS

European Search Report form corresponding European Patent Application No. EP 07124010.5 mailed Apr. 16, 2008.

*Primary Examiner*—Ralph A Lewis
*Assistant Examiner*—Yogesh Patel
(74) *Attorney, Agent, or Firm*—Polster, Lieder, Woodruff & Lucchesi, L.C.

(57) ABSTRACT

A combined irrigator-vacuum device includes a pump assembly mountable over a syringe or device body. The device body has a dividing wall which divides the body into a clean chamber and a waste chamber. Openings are formed at the bottom of the body to provide an inlet into said waste chamber and an outlet from said clean chamber. The pump assembly includes a housing and a compressible cover defining a pump chamber. A vacuum valve and an irrigation valve are positioned within the pump chamber above the syringe waste chamber and clean chamber, respectively. The pump is operable such that compression of the cover causes irrigant fluid to be ejected from the clean chamber and release of the cover causes used irrigant to be vacuumed into the waste chamber. The device can be selectively switchable between an irrigation-vacuum mode, an irrigation-only mode and a vacuum-only mode.

21 Claims, 11 Drawing Sheets

U.S. PATENT DOCUMENTS

| | | | |
|---|---|---|---|
| 5,171,146 A * | 12/1992 | Guerci | 433/81 |
| 5,254,086 A * | 10/1993 | Palmer et al. | 604/38 |
| 6,641,394 B2 * | 11/2003 | Garman | 433/81 |
| 6,907,897 B2 * | 6/2005 | Maula et al. | 137/334 |
| 2003/0031978 A1 * | 2/2003 | Garman | 433/89 |
| 2004/0035886 A1 * | 2/2004 | Cordomi | 222/321.9 |

\* cited by examiner

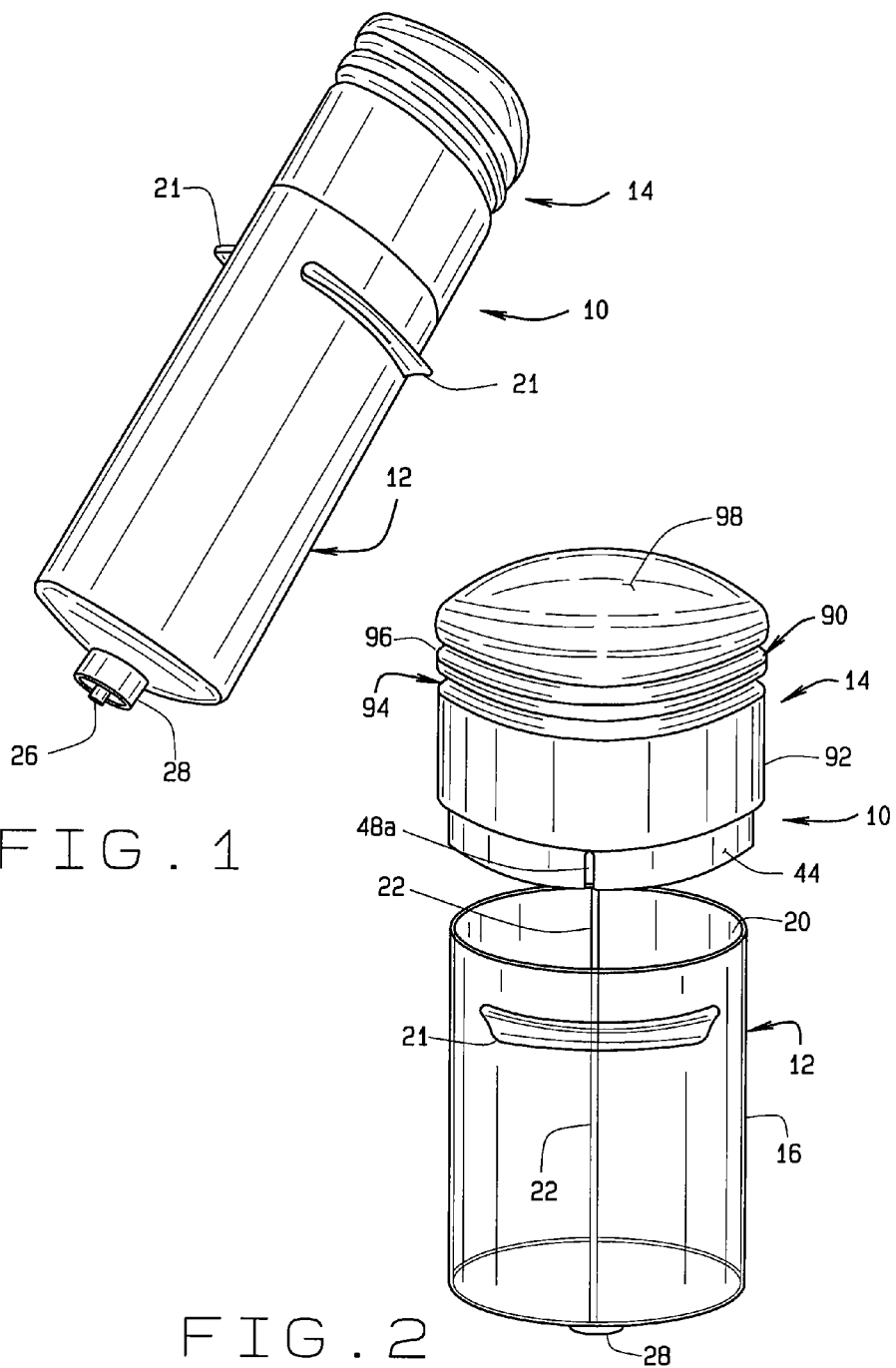

SYRINGE FOR A COMBINED DENTAL IRRIGATOR AND VACUUM DEVICE

CROSS-REFERENCE TO RELATED APPLICATIONS

This application is related to co-pending application Ser. No. 11/618,271 filed Dec. 29, 2006 entitled Cannula For A Combined Dental Irrigator And Vacuum Device, and which is incorporated herein by reference.

STATEMENT REGARDING FEDERALLY SPONSORED RESEARCH OR DEVELOPMENT

Not Applicable.

BACKGROUND OF THE INVENTION

This invention relates to endodontic tools, and in particular, to a combined irrigator and vacuum device. Although the tool is described for use with endodontic procedures, it will be apparent that the combined irrigation valve and vacuum tool can be used for other dental procedures as well.

BRIEF SUMMARY OF THE INVENTION

Following tooth maturation, the dental pulp is harbored within the structural elements of the tooth. Frequently, and for a variety of reasons, the pulp is irreversibly injured, resulting in inflammatory and infectious conditions which often adversely affect the tooth and its supporting structures. Clinically, as an alternative to extraction, root canal treatment is performed and ideally directed towards the elimination of pulp, bacteria, and related irritants from the root canal system, followed by three-dimensionally filling the root canal space with an inert, biocompatible, dimensionally stable, filling material, such as gutta percha. Ideally, the obturation procedures will fill not just the main canal, but the fins, webs, cul-de-sacs, lateral canals, and all portals of exit between the root canal system and the tooth's attachment apparatus.

Central to a successful endodontic (or root canal) treatment has been the use of chemical reagents during mechanical root canal shaping procedures to completely clean all aspects of the root canal system. The chemicals used to enhance canal debridement and disinfection during cleaning and shaping procedures potentially reach all aspects of the root canal system. The most popular chemicals currently used during canal preparation to actively assist in cleaning and disinfecting include bleach, hydrogen peroxide, and chelating agents. Often, a 2%-5% solution of a clear, pale, greenish-yellow strongly alkaline solution of sodium hypochlorite (NaOCl) and ethylenediamine-tetracetic acid (EDTA) are used.

One goal of cleaning and shaping procedures is to three-dimensionally debride all tissue, bacteria when present, and related irritants from the root canal system. During canal preparation, a solution of NaOCl is liberally irrigated into the root canal space where its solvent action facilitates the digestion and elimination of pulp, bacteria, viruses, spores, endotoxins and other irritants generated by the microorganisms (i.e., the bacteria, viruses and spores). This solution has the potential to circulate, penetrate and, hence, clean into all aspects of the root canal space. However, studies have shown that even the most thorough use of sodium hypochlorite does not result in complete debridement of the root canal space.

A second goal of cleaning and shaping procedures is to remove the smear layer from the wall of the prepared canal. The walls of a root canal are comprised of dentin, which contains millions of dentinal tubules per square millimeter. Instruments used to negotiate and shape a canal cut dentin and dentin, in combination with organic substrates, forms dentinal mud. Dentinal mud, pulp, bacteria, and other related irritants have been consistently visualized histologically after shaping procedures in the dentinal tubules and various aspects of the root canal systems. Thus, after cleaning and shaping procedures, the root canal is still covered with a film of debris, frequently described in the literature as a "smear layer." A third goal of endodontic cleaning and shaping procedures is to disrupt and remove biofilms. Biofilms form when bacteria become protected in sticky polysaccharide substrates. Residual bacteria adjust to anaerobic environments, frequently mutate, and invite infection.

After cleaning and shaping, the root canal has been traditionally filled with gutta percha and a root sealer. However, if there is incomplete debridement, or a failure to remove the smear layer or biofilm within the root canal space, then the filling and sealing of the root canal system can be compromised. If obturation is incomplete then the root canal space is predisposed to bacterial leakage and failure. Post-treatment failures attributable to leakage are common and require endodontic retreatment of the tooth or extraction. Thus, to facilitate cleaning, there must be complete debridement and the disruption and removal of the smear layer and biofilm. To enhance prognosis, practitioners use a weak acid or surfactant, such as 17% EDTA, in an effort to enhance three-dimensional cleaning. Typically, the root canal is flushed with EDTA, or other emerging final rinse solutions, to accomplish this.

Flushing of the root canal is generally accomplished using a traditional irrigating syringe which injects an irrigating solution, such as the above noted NaOCl or EDTA solutions, into the root canal. During the cleaning process, residual tissue, bacteria, and related irritants are harbored within the root canal. As can be appreciated, irrigating solutions serve to flush out residual debris. However, irrigating solutions themselves hold a significant amount of residual tissue products, bacteria when present, and dentine mud. As such, repeated flushing is advocated but frequently lacking clinically. Removal of the solution is typically accomplished by attaching various devices on to a high-speed suction line which serves to vacuum the majority of the irrigating solution and hopefully debris from the root canal space. Paper points are used to clinically wick and dry the rest of the prepared canal. In the time it takes to switch from irrigating to vacuum procedures, which require different devices, some of the debris, bacteria, and other elements that the practitioner desires to remove from the canal may settle, making removal of such elements more difficult.

BRIEF SUMMARY OF THE DISCLOSURE

A combined dental irrigation valve-vacuum device made in accordance with the present invention comprises a body and a pump assembly. Illustratively, the body includes a side wall and a bottom, which in combination define a volume. A divider can divide the volume into a clean chamber and a waste chamber. An outlet from the clean chamber and an inlet to the waste chamber are formed in the body bottom. The clean chamber outlet and the waste chamber inlet are spaced apart and isolated from each other. A nose extends from the body bottom and is surrounded by a collar. The nose and collar, in combination, define an annular channel. The nose includes a passage therethrough in communication with one of the clean chamber outlet and waste chamber inlet; and the other of the clean chamber outlet and waste chamber inlet is in opening into the annular channel.

The pump assembly comprises a base assembly and a valve assembly. The base assembly comprises a base surface and a base wall extending downwardly from the base surface. The base wall mates with the body wall to removably hold the base on the body. A pair of spaced apart walls extends down from the bottom of the base surface and across the base. The walls define a slot sized to receive the body divider. The base surface cooperates with the body wall and divider to close the clean and waste chambers and to isolate the clean and waste chambers from each other. Openings are formed in the base surface, there being at least one opening above each of chamber a valve assembly above the base.

The valve assembly comprises a bottom surface and an upwardly extending peripheral wall. An irrigation valve and a vacuum valve are positioned on the valve assembly bottom surface within the perimeter of the peripheral wall. The irrigation valve and a vacuum valve each comprise a stem extending upwardly from the valve assembly bottom surface, a bottom opening in the valve assembly bottom surface at a bottom of the stem, an upper opening at a top of the stem, a valve seat formed within the stem, and a valve element received within the stem. The valve is being movable between a first, closed position in which the valve element engages the valve seat to close the valve and a second, opened position in which the valve element is spaced from the seat. The valve element of each the valve is biased to its closed position.

A compressible cover is received on the valve assembly base to define a pump chamber with the base. The valves are positioned within the pump chamber. The cover is movable between a compressed position and a relaxed position; whereby, when the cover is moved to its compressed position the valve element of the irrigation valve is moved from its closed position to its opened position and when the cover is returned to the relaxed position from the compressed position; the valve element of the vacuum valve is moved from its closed position to its open position. The cover is spring biased to its relaxed position.

In one embodiment, the valve assembly bottom surface is defined by the base assembly surface, such that the base surface and wall and the valve assembly bottom surface and peripheral wall are formed as a unitary one-piece member. In this embodiment, the openings in the base surface define the openings in the valve stems.

In another embodiment, the base assembly and valve assembly are separate, and the valve assembly is rotatable relative to the base assembly. By rotating the valve assembly, the device can be selectively switched between a vacuum mode, an irrigation mode, and an irrigation/vacuum mode. In the irrigation/vacuum mode, the irrigation valve is positioned above the clean chamber, the vacuum valve is positioned above the waste chamber, and the openings at the bottom of the irrigation valve stem and the vacuum valve stem are aligned with the openings in the base surface above the clean chamber and the waste chamber, respectively. In the irrigation-only mode, both the valves are positioned above the clean chamber and the opening at the bottom of the irrigation valve stem is aligned with the opening in the base surface above the clean chamber. In the vacuum-only mode, both the valves are positioned above the waste chamber and the opening at the bottom of the vacuum valve stem is aligned with the opening in the base surface above the waste chamber.

To facilitate rotation of the valve assembly about the base assembly, the base assembly comprises a post extending upwardly from the approximate center of its surface and the valve assembly includes an opening positioned generally in the center of the valve assembly bottom surface through which the base post extends. The valve assembly thus rotates about the base post and the base post defines an axis of rotation for the valve assembly. To further facilitate rotation of the valve assembly and to provide the valve assembly with additional support, the valve assembly can be provided with a tube extending upwardly from the hole in the valve assembly bottom surface, and the base assembly post extends through the valve assembly tube.

To facilitate positioning of the valve assembly, the dental irrigation valve-vacuum device can be provided with indicia on the base assembly and valve assembly. The indicia on the base assembly are indicative of a position to which the valve assembly is to be rotated to place the device in a desired mode of operation.

BRIEF DESCRIPTION OF THE SEVERAL VIEWS OF THE DRAWINGS

FIG. 1 is a perspective view of a first illustrative embodiment of combined irrigator-vacuum device made in accordance with the invention;

FIG. 2 is an exploded view if the irrigator-vacuum device;

Corresponding reference numerals will be used throughout the several figures of the drawings.

DETAILED DESCRIPTION OF THE INVENTION

Figure 3:
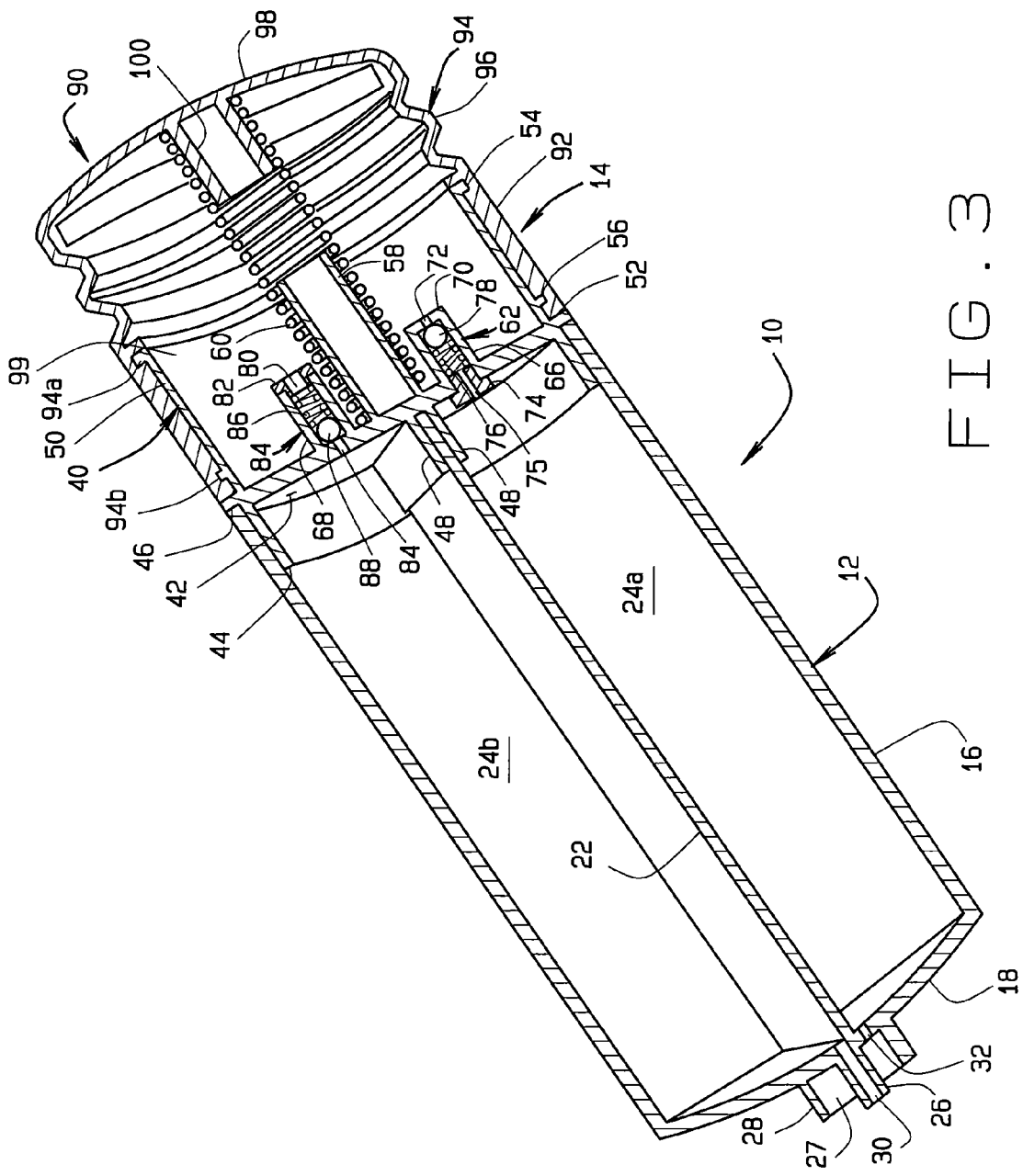
FIG. 3 is a cross-sectional view of the irrigator-vacuum device.

The following detailed description illustrates the invention by way of example and not by way of limitation. This description will clearly enable one skilled in the art to make and use the invention, and describes several embodiments, adaptations, variations, alternatives and uses of the invention, including what we presently believe is the best mode of carrying out the invention. Additionally, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

A first illustrative embodiment of an irrigator-vacuum device 10 made in accordance with the present invention is shown generally in FIGS. 1-4. The device 10 includes a hollow body 12 and a pump assembly 14. The body 12 includes a side wall 16, a bottom 18 and an open mouth or top end 20. The body 20 is shown in FIGS. 1 and 2 to be generally elliptical, by can be any desired shape. Flanges 21 extend from opposite sides of the body side wall 16 to facilitate use of the irrigator-vacuum device 10. Internally, the body 12 includes a separator 22 which divides the hollow body into two chambers 24a and 24b. As will be described below, chamber 24a is a "clean" chamber which holds a supply of fresh irrigant and chamber 24b is a "waste" chamber which stores used irrigant which has been withdrawn from the root canal. As can be appreciated, the used irrigant will contain residual tissue, dentinal mud, biofilm remnants, and other elements which make up the smear layer.

The irrigator-vacuum device 10 includes a central nozzle 26 extending from the bottom 18 of body 12. The nozzle 26 is surrounded by a collar 28, and hence the post and collar, in combination, define an annular area 27. The nozzle 26 is hollow, and defines a passage 30 which extends through the body bottom 18 and opens into the waste chamber 24b. A second opening 32 in the body bottom is positioned between the nozzle 26 and the collar 28 and opens into the clean chamber 24a, thereby placing the annular area 27 in fluid communication with the clean chamber 24a. The nozzle 26 is generally centered relative to the body bottom 18. Hence, the dividing wall 22 is slightly off set from the center of the body, such that one chamber is larger than the other.

Figure 4:
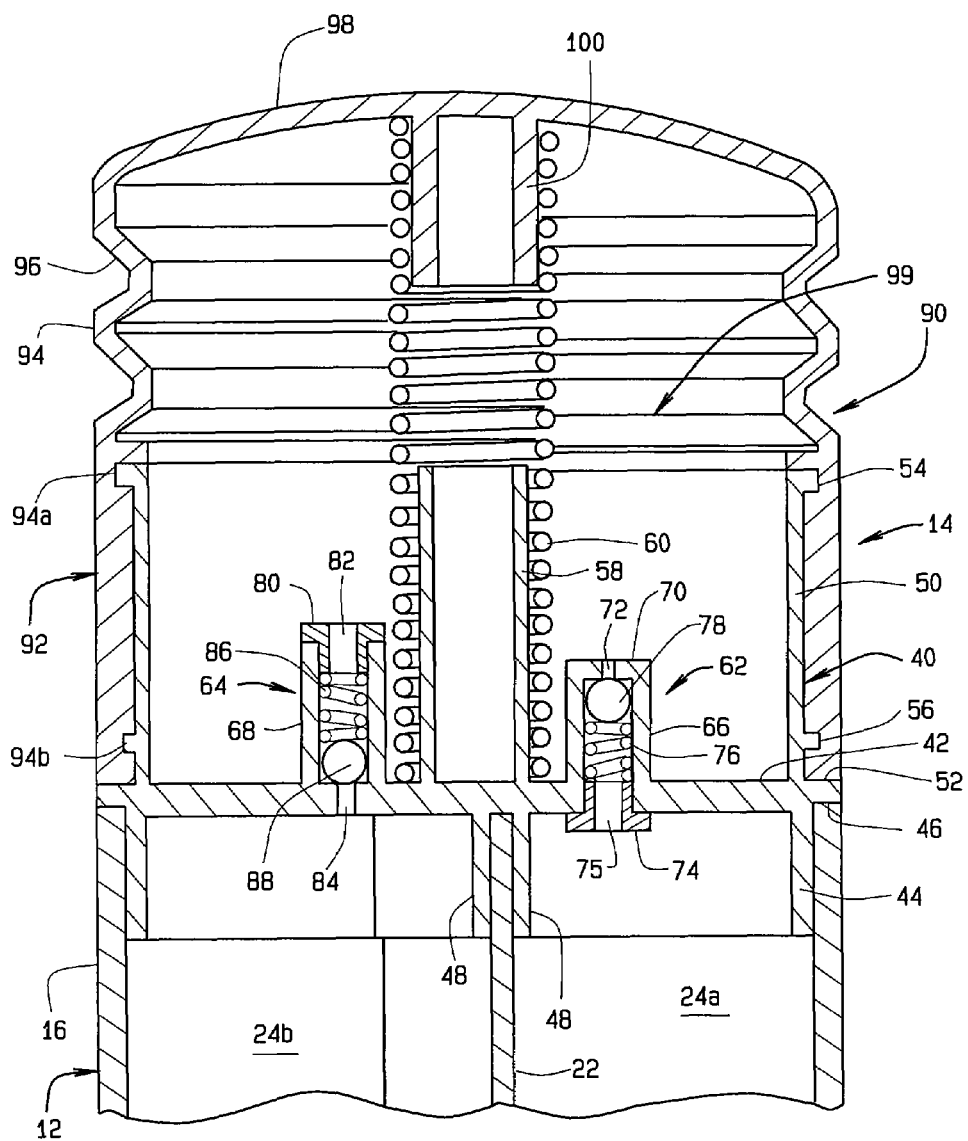
FIG. 4 is an enlarged cross-sectional view of a pump assembly for the irrigator-vacuum device.
Figure 5:
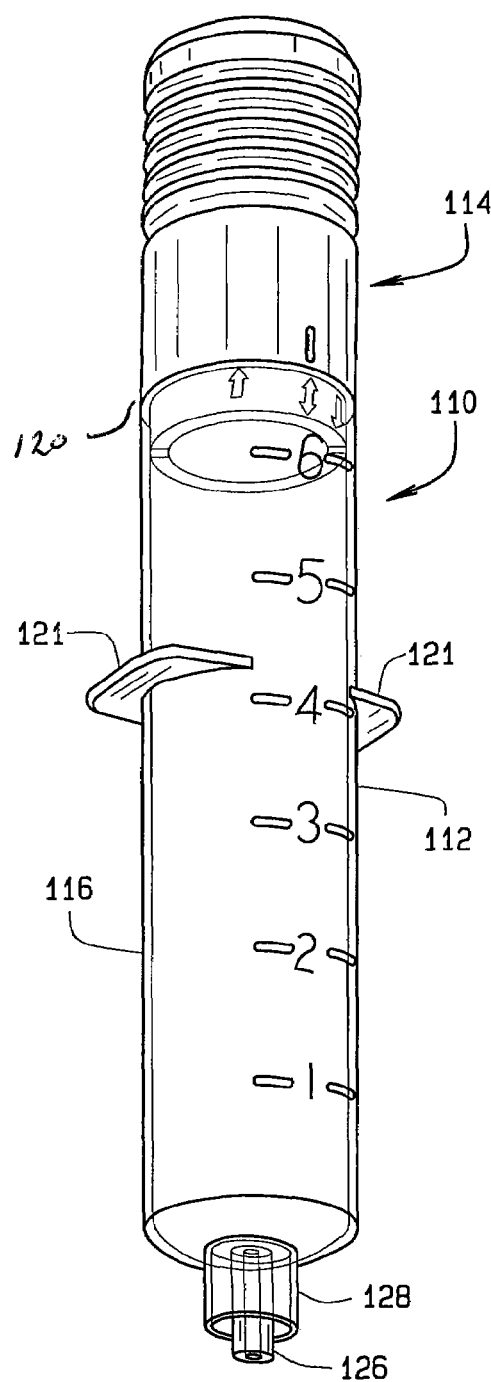
FIG. 5 is a perspective of a second illustrative embodiment of a combined irrigator-vacuum device made in accordance with the present invention.

Turning to FIG. 4, the pump assembly 14 includes a housing 40 having a base 42 sized and shaped complimentarily to the body side wall 16, such that the base 42 will cover the top surface of the body side wall 16. That is, the peripheral edge of the base 42 is generally flush with the outer surface of the syringe body side wall 16. A lower wall 44 extends downwardly from a bottom surface of the base 42. The lower wall 44, like the base 42, is shaped complimentarily to the body side wall 16. However, the lower wall 44 is sized to be received within the body side wall 16. Thus, the lower wall 44 is spaced inwardly slightly from the periphery of the base 42 to form a slight shoulder 46 which rests on the body side wall 16. A pair of spaced apart ribs 48 extends across the base bottom surface and defines a slot 48a therebetween. The ribs 48 are positioned, and spaced apart a distance sufficient, such that when the pump assembly 14 is placed on the body 12, the body separator 22 will be received in the slot 48a defined by the ribs 48. Thus, the pump base 42, the wall 44 and the ribs 48 close the chambers 24a,b and also effectively isolate the chambers 24a,b from each other, such that fluid from one chamber cannot migrate to the other chamber. Hence, the clean chamber 24a and the waste chamber 24b are sealed relative to each other.

The pump housing 40 further includes an upper wall 50 extending upwardly from an upper surface of the pump base 42. The upper wall 50 is shaped correspondingly to the body side wall 16 and the pump base 42, but is spaced inwardly slightly from the edge of the base 42 to define a seat 52. Upper and lower ribs 54, 56 extend around the outer surface of the wall 50. At the approximate center of the base 42, the pump assembly 14 includes a post 58. A coiled spring 60 surrounds the post 58. In its relaxed state the spring 60 is longer than the post 58 is tall.

Irrigate and vacuum valves 62 and 64 are positioned on opposite sides of the post. The irrigation valve 62 is positioned over the clean chamber 24a and the vacuum valve 64 is positioned over the waste chamber 24b. The valves 62, 64 each include a hollow stem 66, 68, respectively. The stem 66 of valve 62 has an upper surface 70 having an opening 72 therethrough. At its bottom end, the stem 66 opens into the chamber 24a. A retainer or plug 74 having an opening 75 therein is received in the opened bottom of the stem. A spring 76 and ball 78 are received within the stem 66. As seen, the spring and ball are positioned such that the spring normally urges the ball against the stem upper surface 70 to close the opening 72. As will become clear, the opening 75 defines an outlet to the irrigation valve 62, the opening 72 defines an inlet to the irrigation valve 62, and the upper surface 70 defines a valve seat surrounding the inlet, and the ball 78 defines a valve member.

The vacuum valve 64 is substantially similar to the irrigation valve 62, but is constructed in reverse. The stem 68 of vacuum valve 64 is opened at its top end to receive a plug 80 having an opening 82 therethrough. An opening 84 is formed in the pump base 42 within the stem 68 to place the stem in communication with the waste chamber 24b. A spring 86 and ball 88 are received within the stem 66. As seen, the spring and ball are positioned such that the spring normally urges the ball against the upper surface of the 44 within the stem to close the opening 84. As will become clear, the opening 82 defines an outlet to the valve 64, the opening 84 defines an inlet to the irrigation valve 64, and the base 42 within the stem 66 defines a valve seat surrounding the inlet, and the ball 88 defines a valve member.

Although the valve stems 66 and 68 are formed oppositely from each other—that is, the valve stem 66 receives the plug 74 at its bottom and the valve stem 68 receives the plug 80 at its top, it will be apparent that the two valve stems can be formed in the same manner, such that both valve stems receive their respective plugs at the top or the bottom. As will be appreciated, this will allow for the springs and balls for the valves 62 and 64 to both be inserted from one side of the base 42.

The pump assembly 14 also includes a cover 90. The cover 90 includes a lower portion 92 which is received about the pump body wall 50. To this end, the cover 90 includes a pair of internal grooves 94a,b which receive the ribs 54 and 56. The ribs 54 and 56 and the grooves 94a,b form an interference fit which prevents inadvertent removal of the pump cover 90 from the pump housing 40. The cover 90 also includes an upper portion 94 having a collapsible wall 96 and a top 98. To enable the wall 96 to be collapsible, the wall 96 is accordioned, as seen in FIGS. 2-4. A post 100 extends downwardly from the inner surface of the cover top 98. The post 100 is positioned to be aligned with the pump housing post 58 and to receive the top end of the spring 60.

The pump cover 90 and pump housing 40, in combination define an enclosed pump chamber 99. As can be appreciated, the pump chamber 99 is placed in communication with the chambers 24a,b of the irrigator-vacuum device body by means of the valves 62 and 64.

In operation, when the cover 90 is compressed, the pump chamber 99 will become smaller increasing the pressure within the chamber 99. The increased pressure will force the valve balls 78 and 88 downwardly. As can be seen, this will open the irrigation valve 62 (to place the pump chamber 99 in communication with the clean chamber 24a through the valve inlet 72 and valve outlet 75) and will reinforce the closing of the vacuum valve 64 by urging the vacuum valve ball 88 against the valve seat. Thus, when the cover is compressed, the pump chamber 99 and hence the clean chamber 24a will become pressurized to force at least a portion of the contents of the clean chamber to exit the irrigator-vacuum device 10 through the opening 32 at the bottom of the device body 12. Conversely, when the cover is released, the spring 60 (which will have been compressed) will force the cover up, thereby expanding the pump chamber 99. As can be appreciated, this will result in a drop in pressure in the pump chamber 99. This drop in pressure is sufficient to overcome the force of the spring 86 of the vacuum valve 64. Additionally, when the cover is released, the spring 76 of the irrigation valve 62 will force the valve ball 78 upwardly to close the irrigation valve 62. At the same time, the reduced pressure within the pump chamber 99 will allow for the vacuum valve 64 to open against the force of the spring 86, to allow fluid to enter the waste chamber 24b through the passage 30 at the bottom of the device body 12. Thus, when the cover 90 is released, fluid from the root canal will be vacuumed up to be stored in the waste chamber 24b of the device body 12.

Hence, by compressing the cover 90, the device 10 operates as an irrigator; and by releasing the cover 90, the device 10 operates as a vacuum. Due to the operation of the valves 62 and 64, the practitioner can, by pressing the cover 90, irrigate the canal with a predetermined amount of irrigant, which is preferably less than the amount of irrigant contained within the clean chamber 24a. Similarly, be releasing the cover, the practitioner can vacuum waste or used irrigant from the root canal and store the used irrigant in the waste chamber 24b. The amount of irrigant forced from the device 10 or vacuumed into the device 10 is determined by the size of the pump chamber 99. The cover 90 can be sized to form a pump chamber 99 of a size which will force or vacuum a predetermined and set amount of irrigant from or into the device 10. Again, and due to the operation of the valves 62 and 64, if both chambers have fluid in them, pressing of the cover 90 will not release used irrigant from the waste chamber 24b. Hence, used irrigant will not be forced back into the root canal when the pump cover 90 is depressed. Thus, a practitioner can use a single tool (i.e., the device 10) to both irrigate and vacuum a root canal.

The irrigator-vacuum device 10 operates only in a combined irrigation and vacuum mode. That is, each time the pump cover is compressed to release irrigant into a root canal, the release of the cover 90 results in a vacuum of the irrigant from the root canal. The irrigator-vacuum device 110 of FIGS. 4-11B, on the other hand, is switchable between a vacuum-only mode (in which case, activation of the pump only activates the vacuum side of the device 110), an irrigation-only mode (in which case, activation of the pump only activates the irrigation side of the device 110), and a combined irrigation and vacuum mode with operates like the device 10, that is, for each press and release of the cover, the pump first irrigates and then vacuums.

The device 110 is shown generally in FIGS. 5-8 and in its three different modes of operation in FIGS. 9A-C. The components of the pump assembly for the device 110 are shown in more detail in FIGS. 10A-13B. The device 110 includes a hollow body 112 and a pump assembly 114. The body 112 includes a side wall 116, a bottom 118 and an open mouth or top end 120. Flanges 121 extend from opposite sides of the body wall 116 to facilitate use of the irrigator-vacuum device 110. Internally, the body 112 includes a separator 122 which divides the hollow body into two chambers 124a and 124b. As will be described below, chamber 124a is a "clean" chamber and chamber 124b is a "waste" chamber.

Figure 6:
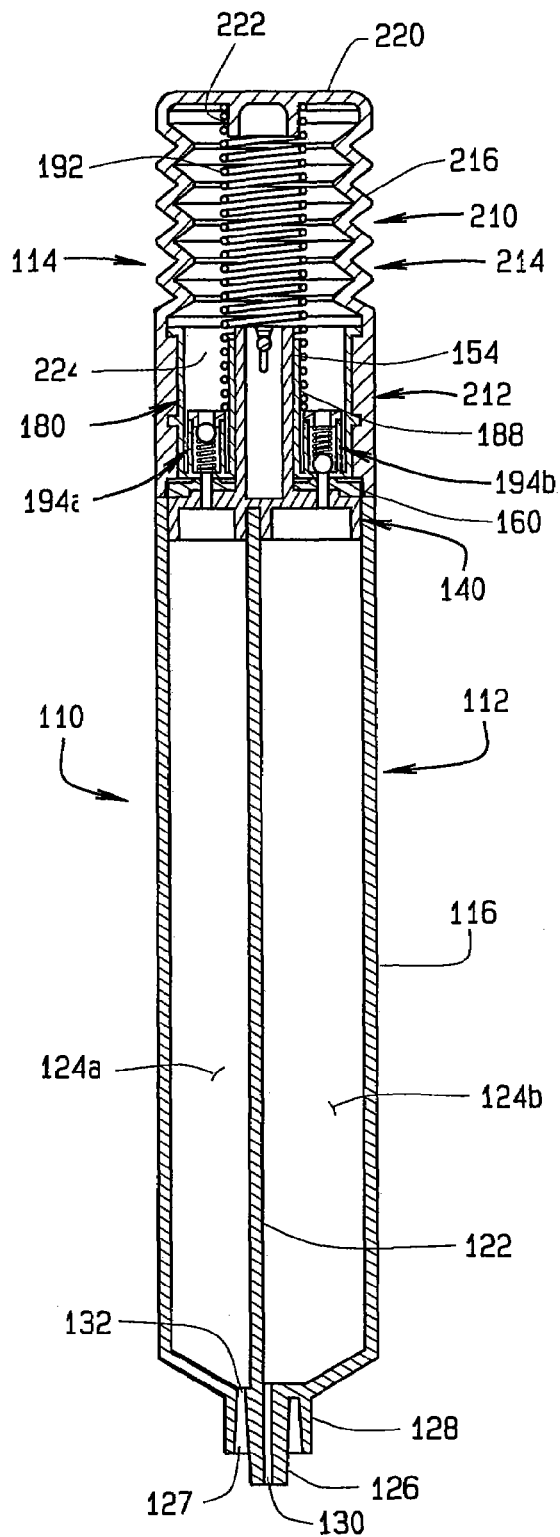
FIG. 6 is a vertical cross-sectional view of the irrigator-vacuum device of FIG. 5.
Figure 7:
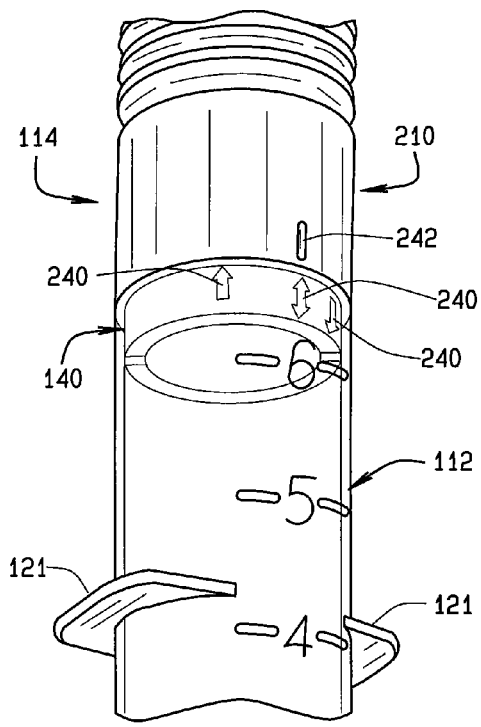
FIG. 7 is an enlarged perspective view of an upper end of the irrigator-vacuum device of FIG. 5.
Figure 8:
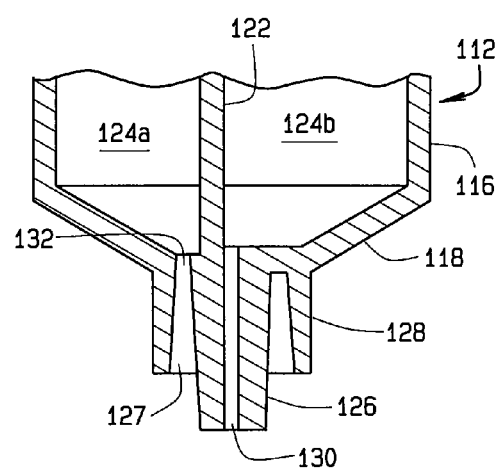
FIG. 8 is an enlarged cross-sectional view of a bottom end of the irrigator-vacuum device.

As seen more clearly in FIGS. 6 and 8, the irrigator-vacuum device 110 includes a central nozzle 126 extending from the bottom 118 of body 112. The nozzle 126 is surrounded by a collar 128, and hence the nozzle and collar, in combination, define an annular area 127. The nozzle 126 is hollow, and defines a passage 130 which extends through the body bottom 118 and opens into the waste chamber 124b. A second opening 132 in the body bottom is positioned between the nozzle 126 and the collar 128 and opens into the clean chamber 124a, thereby placing the annular area 127 in fluid communication with the clean chamber 124a.

Turning to FIGS. 9A-13B, the pump assembly 114 includes a base member 140, a seal member 160, a valve assembly 180 and a cover 210. The base member 140 is shown in greater detail in FIGS. 11A-D. The base member 140 comprises a plate 142 shaped complimentarily to the body wall 116, and sized to be received within the body wall 116. A base wall 144 extends downwardly from a bottom surface of the base plate 142. The base wall 144 is shaped complimentarily to the body wall 116 and is sized to be received within the body wall 116. A pair of spaced apart walls 148 extends across the bottom surface of the plate 142 and defines a channel 148a therebetween. The walls 148 are positioned, and spaced apart a distance sufficient, such that when the pump assembly 114 is placed on the body 112, the body separator 122 will be received in the channel 148a. Thus, the pump base plate 142 and walls 144 and 148 close the chambers 124a,b and also effectively isolate the chambers 124a,b from each other, such that fluid from one chamber cannot migrate to the other chamber. Hence, the clean chamber 124a and the waste chamber 124b are sealed relative to each other.

Figures 11A, 11B:
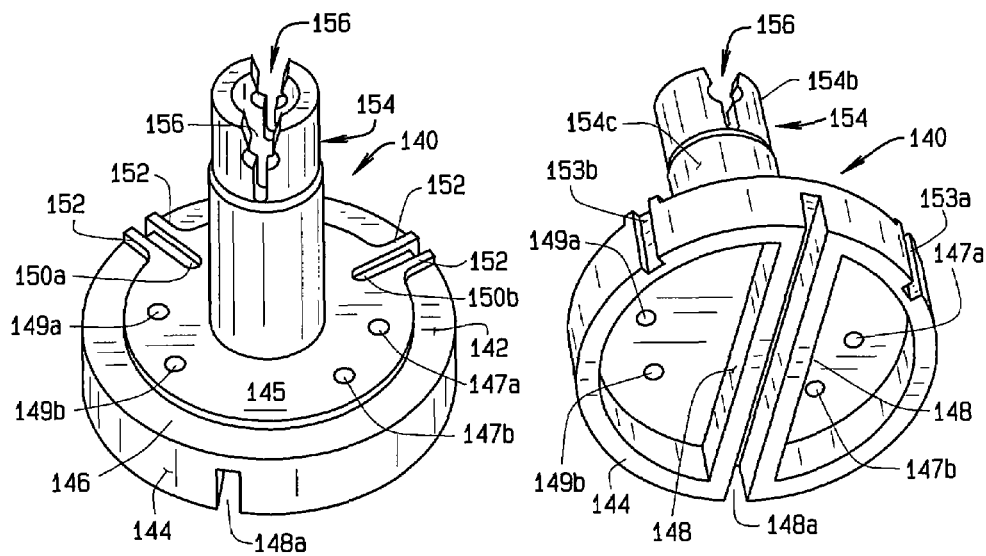
FIGS. 11A-D are top perspective, bottom perspective, side elevational and top plan views, respectively, of a base of the valve assembly.
Figures 11C, 11D:
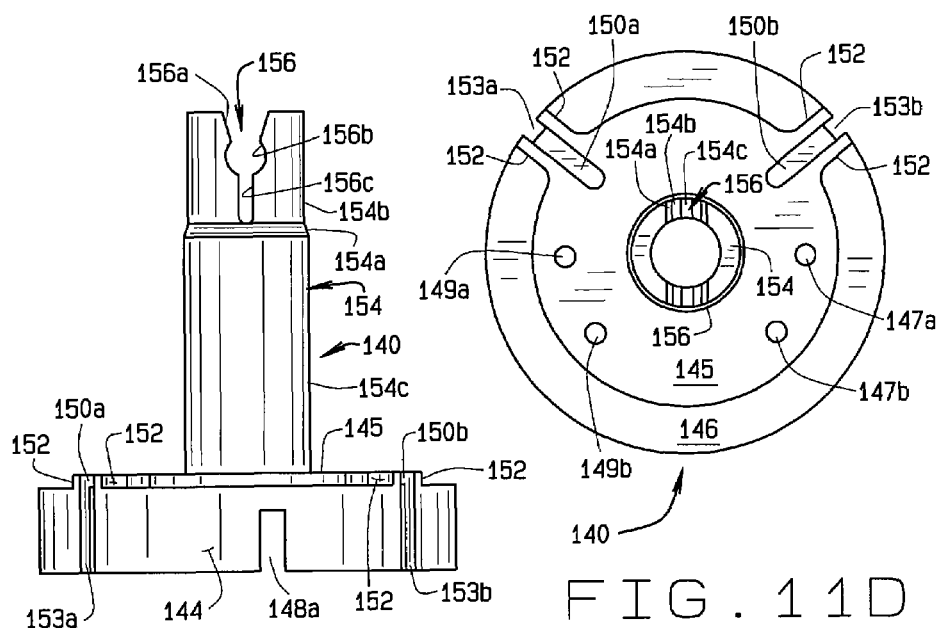
Figure 12A:
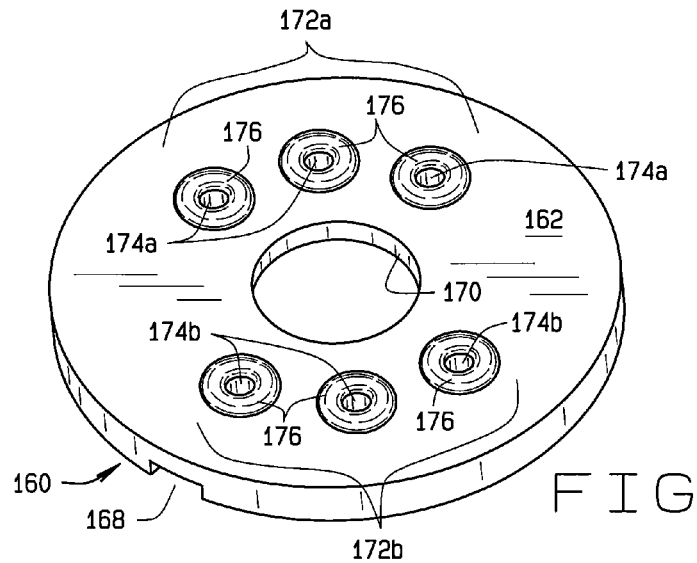
FIGS. 12A-C are top perspective, bottom perspective and side elevational views, respectively, of a seal of the pump assembly.
Figure 12B:
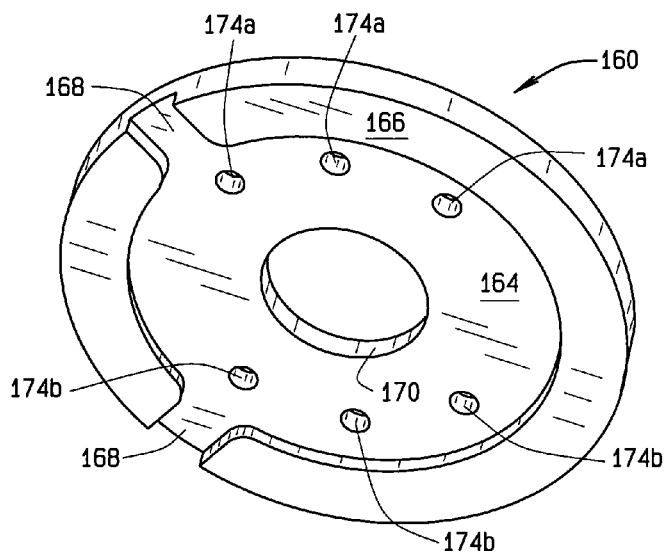
Figure 12C:
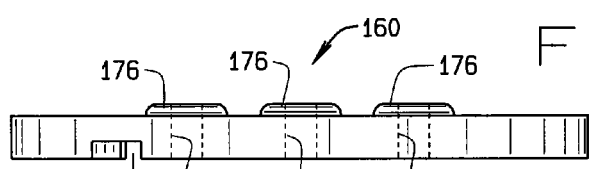
Figure 13A:
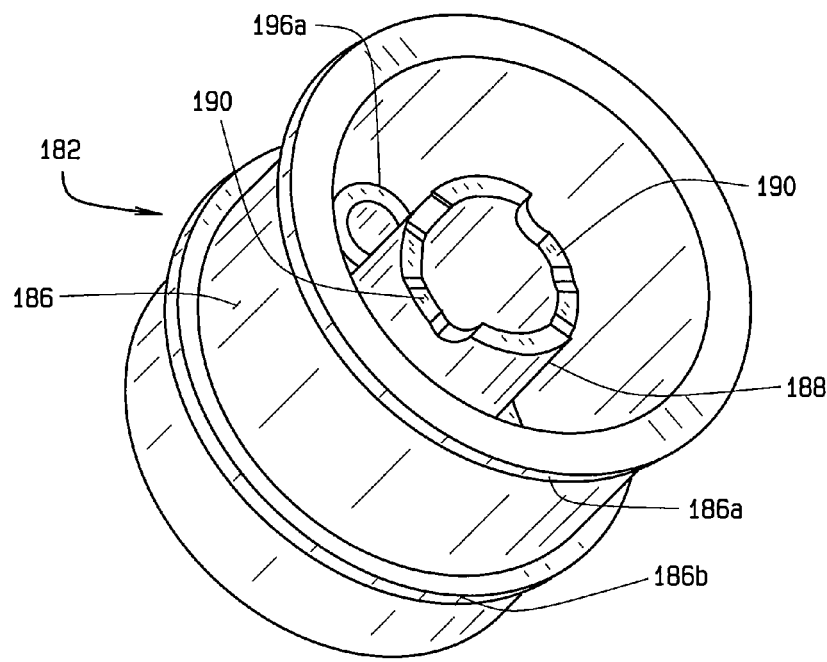
FIGS. 13A-B are top perspective and top plan views of a valve body of the pump assembly.
Figure 13B:
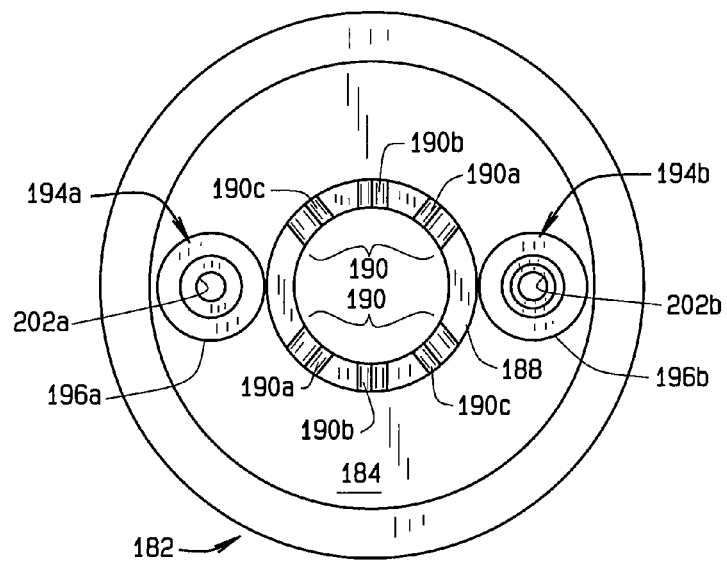

A raised platform 145 extends upwardly form the top of the base plate 142. The platform 145 is generally centered with respect to the plate 142 and has a circumference smaller than that of the base plate, such that the plate 142 and the platform 145 define a shoulder 146 which extends substantially about the periphery of the base plate. Two sets of holes 147a,b and 149a,b extend through the base plate 142 and platform 145. As seen in FIGS. 11A-C, the holes 147a,b and 149a,b open into the clean and waste chambers 124a,b, respectively. Additionally, channels 150a,b extend radially inwardly from the edge of the platform 145. The channels 150a,b are effectively extended to the edge of the plate 142 by walls 152 which extend from the edge of the platform 145 to the edge of the plate 142. As best seen in FIGS. 11B and C, channels 153a,b extend axially along the of the plate wall 144. The channels 153a,b intersect with the channels 150a,b, respectively, to form an L-shaped channel which extends outwardly from an annular midpoint of the platform 145 to the edge of the plate 142 and then down the plate wall 144.

The channels 150a,b are generally radially extending channels and are spaced apart by about 100°. The channel 150a and the holes 147a,b are equally spaced apart, being separated from each other by about 40°. Similarly, the channel 150b and the two holes 149 are equally spaced apart, again, being separated by from each other by about 40°. The radially innermost points of the channels 150a,b and the holes 147 and 149 lie on a circle. The radially innermost points of the channel 150a and the two holes 147 define an arc of about 80°; and the channel 150b and the two holes 149 define an arc of about 80°. As best seen in FIG. 11D, the holes 147a and 149a are opposite each other; the hole 147b is opposite the channel 150a; and the hole 149b is opposite the channel 150b.

Figure 9:
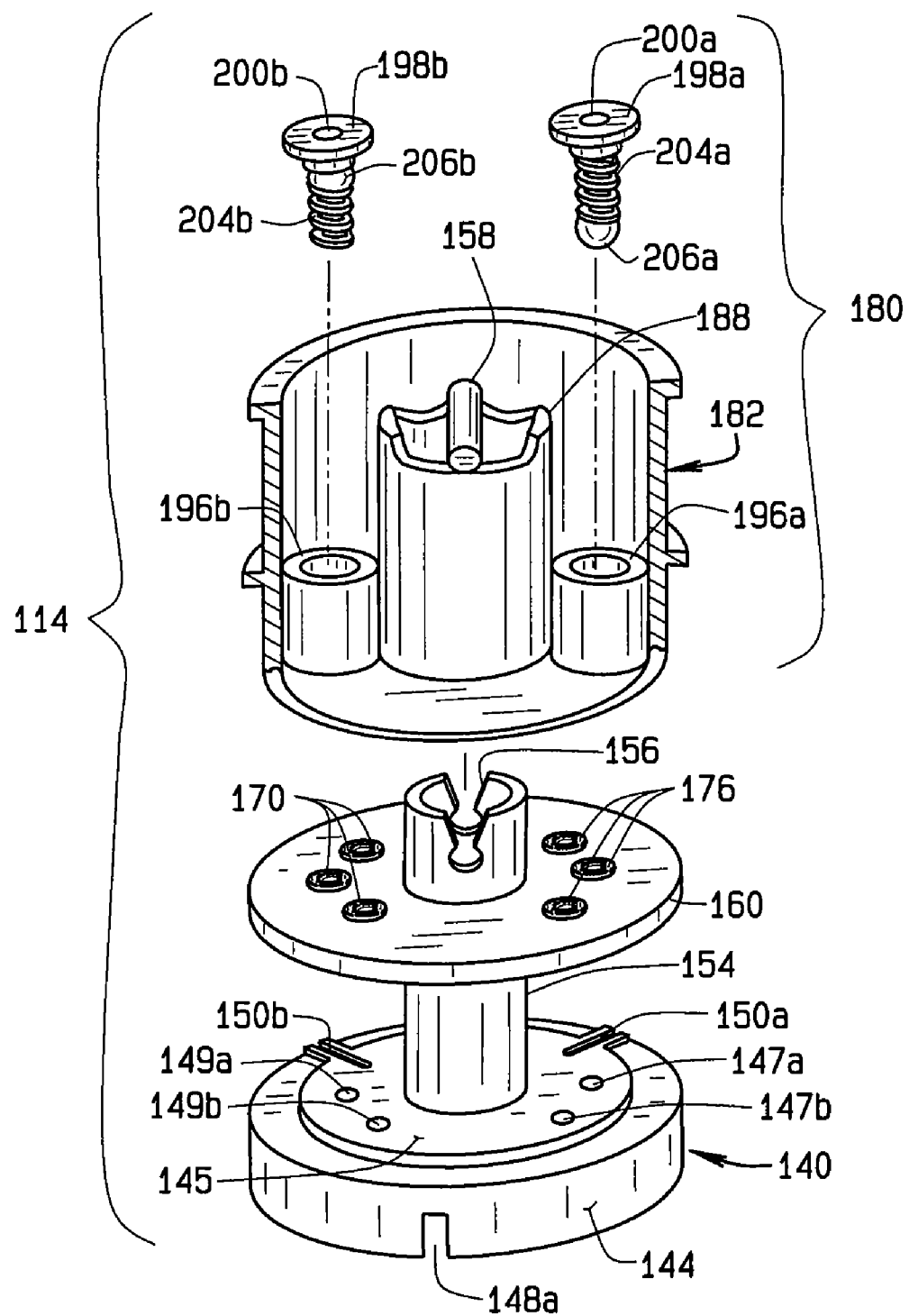
FIG. 9 is an exploded perspective view of the pump assembly with the pump cover removed.
Figure 10A:
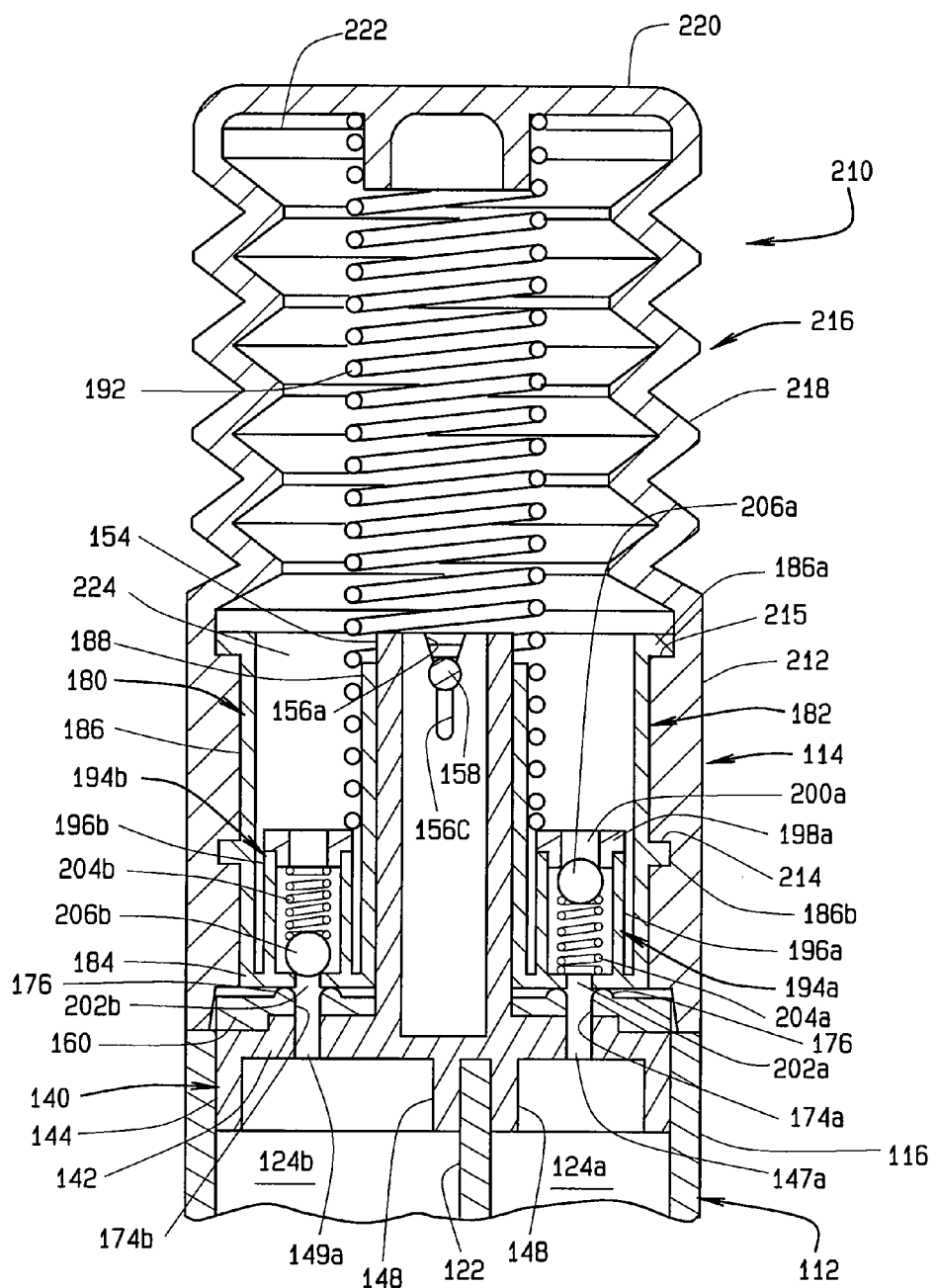
FIGS. 10A-C are enlarged vertical cross sectional views of the pump assembly of the irrigator-vacuum device in an irrigating/vacuum mode (FIG. 10A), an irrigation-only mode (FIG. 10B) and a vacuum-only mode (FIG. 10C)
Figure 10B:
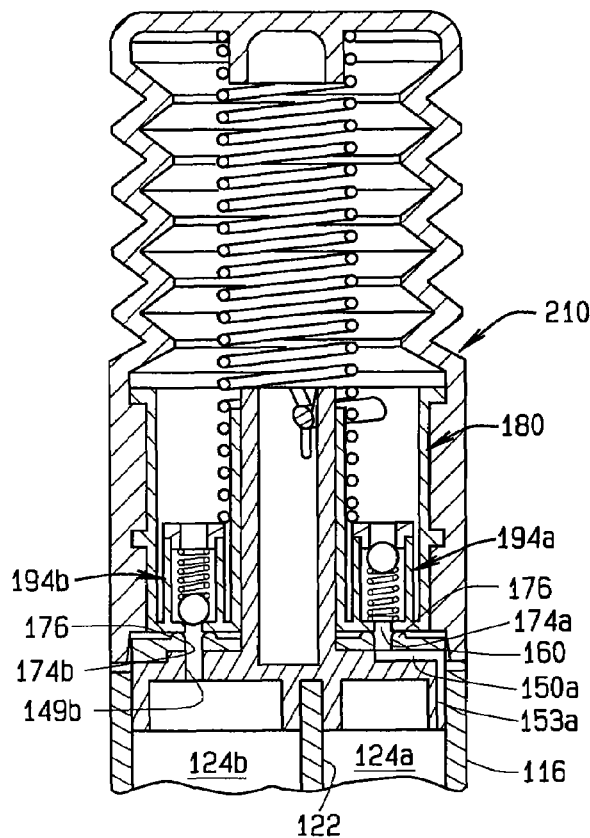
Figure 10C:
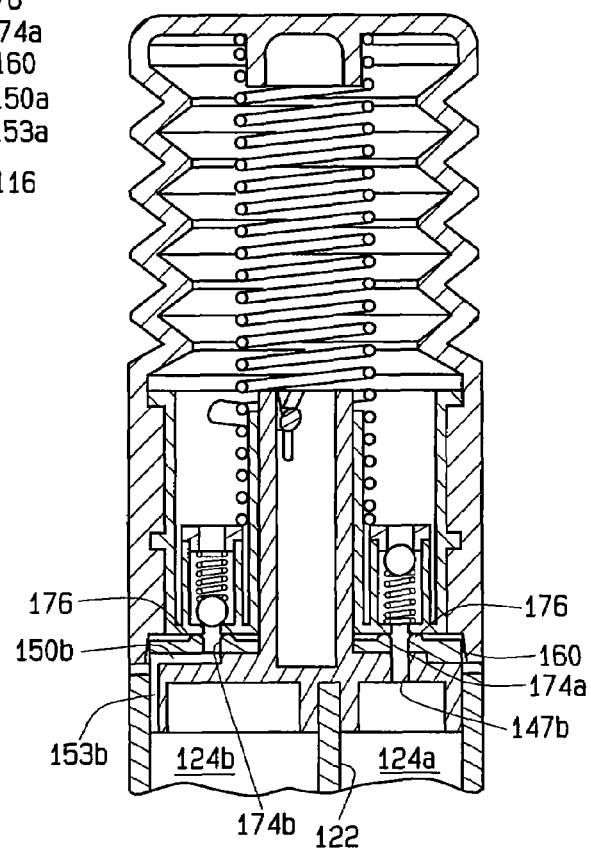

A hollow post 154 extends upwardly from the center of the platform 145. The post is necked down, as at 154a to define a top section 154b which is slightly smaller in circumference than the lower section 154c. Opposed slots 156 extend downwardly from the top surface of the post. The slots 156 each have an upper, generally V-shaped portion 156a which opens into a circular portion 156b. The circular portion 156b then opens into a generally straight portion 156c. The straight portion 156c ends just above the neck 154a of the post 154. The slot 156 receives a dowel rod 158 (FIGS. 9-10C). The dowel rod 158 has a length greater than the diameter of the post 154 and a circumference such that it can be received and tightly held in the circular section 156b of the slot 156. The top V-shaped portion is shaped to allow the dowel to be inserted into the slot, and the length of the slot straight potion 156c allows for the post upper section 154b to flex sufficiently to allow the dowel rod 158 to be pressed into the slot circular section 156b. This allows for the dowel rod to be "snap fit" into the slot circular section 156b. Alternatively, the post 154 could be provided with an opposed pair of holes through which the dowel rod 158 could be axially slid.

A seal member 160 (FIGS. 12A-C) is received on the pump assembly base 140. The seal member 160 is shaped correspondingly to the base plate 140, and hence, is generally circular in plan view. The seal member 160 has a top surface 162 and a bottom surface 164. A wall 166 extends downwardly from the bottom surface 164 at the periphery of the seal member 160. The wall 166 has an annular width and a height approximately equal to the annular width and height of the base shoulder 146 so as to be received on the base shoulder, as seen in FIGS. 10A-C. A pair of slots 168 are formed in the seal wall and are sized and positioned to receive the walls 152 which define the extension of the base member channels 150a,b to the edge of the base member plate 142. Thus, as seen in FIGS. 10B and C, the channels 150a,b are opened beneath the seal member 160 when the seal member 160 is placed on the base member 140. The seal member includes a central opening 170 sized to receive the base member post 154. Lastly, the seal member includes two sets 172a,b of three openings 174a,b each. Each opening 174a,b is surrounded by a raised sealing portion 176 on the seal member upper surface 162. The openings 174a are positioned to be aligned with the holes 147a,b and the channel 150a; and the openings 174b are positioned to be aligned with the holes 149a,b and the channel 150b.

A valve assembly 180 (FIGS. 13A-B) is mounted on the pump base member 140 and seal member 160 for rotation about the pump base and seal member. The valve assembly 180 comprises a housing member 182 having a bottom 184 and a peripheral wall 186 extending upwardly from the bottom 184. The wall 186 is shaped correspondingly to the body wall 116, but is spaced inwardly from the wall 116. Upper and lower ribs 186a,b extend around the outer surface of the wall 186. At its approximate center, the valve housing 182 includes a post 188 which is sized to receive the base post 154. The valve housing post 188 is generally cylindrical in shape and of a generally constant diameter. Opposed cut-out sections 190 are formed in the top edge of the valve housing post 188. The cut out sections 190 define three pair of opposed depressions 190a-c. The depressions 190a-c are sized to receive the dowel rod 158. As will be explained in more detail below, the cut-out sections 190 and their depressions 190a-c co-act with the dowel rod 158 to define discreet stops for the valve assembly 180 as it is rotated relative to the pump base member 140.

Turning to FIG. 10A, a coiled spring 192 surrounds the valve housing post 188. In its relaxed state, as seen in FIG. 6, the spring 192 extends above the tops of the posts 154 and 188. Irrigate and vacuum valves 194a,b are positioned on opposite sides of the post 188. The irrigate and vacuum valves 194a,b each include a hollow stem 196a,b extending upwardly from the valve housing bottom surface 184. The stems 196a,b are open at their tops, and are closed by plugs or covers 198a,b. The plugs each have a passage 200a,b extending through them. Additionally, openings 202a,b are formed in the bottom surface 152 within the stems 196a,b. The stems 196a,b receive springs 204a,b and balls 206a,b. The ball 206a and spring 204a of irrigation valve 194a are positioned such that the spring 204a normally biases the ball 206a upwardly against the plug passage 200a. Hence, the plug 200a defines a valve seat for the irrigation valve 194a. The ball 206b and spring 204b of vacuum valve 194b are positioned inversely relative to the irrigation valve 194a. In the vacuum valve 194b, the ball 206b is biased downwardly by the spring 204b to normally close the opening 202b at the bottom of the stem 196b. Hence, the stem bottom (or more accurately, the valve housing bottom 184 within the valve stem) defines a valve seat for the vacuum valve 194b.

The pump assembly 114 also includes a cover 210. The cover 210 includes a lower portion 212 which is received about the valve assembly housing wall 186. To this end, the cover 210 includes a groove 214 and a shoulder 215 which receive the ribs 186b and 186a, respectively. The rib 186a is received in the groove 214 and the rib 186b sits on the shoulder 215 thereby forming an interference fit between the cover 210 and the valve housing wall 186 to prevent inadvertent removal of the pump cover 210 from the pump valve assembly 180. The cover 210 also includes an upper portion 216 having a collapsible wall 218 and a top 220. To enable the wall 218 to be collapsible, the wall 218 is accordioned, as seen in FIGS. 10A-C. A post 222 extends downwardly from the inner surface of the cover top 220. The post 222 is positioned to be aligned with the pump body post 154 and to receive the top end of the spring 192. As seen in FIGS. 10A-C, the spring 192 is sandwiched between the cover top 220 and the valve stem caps or plugs 198a,b, and is maintained in position with the pump by being received about the cover post 222 and the valve housing post 188. The pump cover 210 and pump valve housing 182, in combination, define an enclosed chamber 224.

The operation of the irrigation/vacuum device 110 and the manner of switching between its three modes of operation will be described in conjunction with FIGS. 10A-C. In FIG. 10A, the pump assembly is shown in its irrigate-vacuum mode. In this position, the irrigation valve 194a is shown as being positioned to be in alignment with the hole 147a above chamber 124a and the vacuum valve 194b is positioned to be in alignment with the hole 149a above the chamber 124b. Further, the valves 194a,b are aligned with the openings 174a,b in the seal member 160. The raised portion 176 surrounding the seal member openings 174a,b seals against the underside of the valve housing surface 184, such that the communication of the valves 194a,b with the chambers 124a,b through the seal member 160 and the base member 140 is sealed and not open to the atmosphere. In this position, the device 110 will operate substantially identically to the device 10. That is, it is in an irrigation/vacuum mode wherein when the when the cover 210 is compressed, the device will eject irrigant from the chamber 124a, and when the cover is released, the device will vacuum used irrigant into the chamber 124b. However, as noted above, the device 110 can be operated in a vacuum-only mode or an irrigation-only mode. This is accomplished by the two-part pump assembly 114. As noted above, the valve assembly 180 is rotatable relative to the base 140.

By rotating the valve assembly in one direction, clockwise, for example, the valves 194a,b will be rotated from their positions shown in FIG. 10A to their positions shown in FIG. 10B. As seen in FIG. 10B, the vacuum valve 194b is aligned with the hole 149b in the base member 140 and is in communication with the waste chamber 124b through the seal member opening 174b and the base member hole 149. The irrigation valve 194a, however, positioned above, and is in communication with the channel 150a and is thus placed in communication with the atmosphere through the channels 150a and 153a. In this position (which is a vacuum-only position), the irrigation valve 194a does not communicate with the clean chamber 124a. Hence, in this positioned, when the cover 210 is compressed, the irrigation valve 194a will not be operable to force irrigant from the chamber 124a. However, the vacuum valve 194b is in communication with the waste chamber 124b and is operable to pull irrigant into the waste chamber 124b. Hence, when the cover 210 is compressed, nothing will happen (that is, no irrigant will be ejected from or vacuumed into the chambers 124a,b, respectively). However, when the cover 210 is released after being compressed, the expansion of the pump assembly chamber 224 will open the waste valve 194b to allow used irrigant to be vacuumed up into the waste chamber 124b from the root canal.

When the valve assembly is rotated in the opposite direction, counter-clockwise, for example, to the position shown in FIG. 10C, the irrigation valve 194a will be in communication with the clean chamber 124a through the hole 147b in the base member 140 and the vacuum valve 194b is above and in communication with the channel 150b to be open to the atmosphere. In this positioned, when the cover 210 is compressed, the valve 162a will be operable to force irrigant from the clean chamber out the opening 132 in the bottom of the syringe body 112. However, because the vacuum valve 194b is in communication with the atmosphere, when the cover 210 is released, the valve 194b will not be operable to vacuum used irrigant from the root canal into the waste chamber 124b.

Hence, when the device is in the irrigation mode (FIG. 10C), each press and release of the cover 210 will result in an ejection of a predetermined amount of irrigant from the clean chamber 124a, and nothing will be vacuumed in to the "waste" chamber 124b. Conversely, when the device is in the vacuum mode (FIG. 10B), each press and release of the cover 210 will result in vacuuming of a predetermined amount of used (or "waste") irrigant from the root canal into the "waste" chamber 124b. Although the device 110 is described as rotating the pump assembly clockwise to switch it to from the irrigation/vacuum mode to the vacuum-only mode and counter-clockwise switch it to the irrigation-only mode; it will be appreciated that, if the chambers (or valves) were reversed, then the pump assembly would be moved in the opposite directions to switch the device 110 between its three modes.

As seen from FIGS. 10A-C, the seal member 160 engages the underside of the valve housing 182 such that the openings 202a,b to the valve stems 196a,b are sealed irrespective of the position of the valve assembly 180. As seen, the seal member 160 engages the valve housing at only six spots, thereby minimizing the contact of the seal member 160 with the valve housing 182. This will tend to reduce the friction between the seal member and valve housing to facilitate rotation of the valve housing to move the valve assembly between the different positions.

To facilitate the positioning of the cover, the base member 140 is provided with indicia 240 (FIG. 7) indicative of the operation of the device at the various settings. Thus, an up arrow "↑" is provided to indicate the position for the vacuum-only mode; a down arrow "↓" is used to indicate the position for the irrigation-only mode; and a dual arrow "↕" is used to indicate the position for the irrigation/vacuum mode. The cover 210 has indicium 242 which is aligned with the indicia 240 of the base member 140 to position the device 110 in the desired mode of operation.

As various changes could be made in the above constructions without departing from the scope of the invention, it is intended that all matter contained in the above description or shown in the accompanying drawings shall be interpreted as illustrative and not in a limiting sense. For example, the tube or post 188 of the valve assembly 180 could be omitted, in which case, the pump assembly base post 154 would extend through the opening in the bottom of the valve assembly bottom surface 184. Alternatively, the posts 154 and 188 could be replaced with a circular groove and a circular rib. Other configurations could also be used to rotatably mount the valve assembly 180 over the base member 140. The clean and waste chambers 24a,b and 124a,b within the body 12, 112 could be switched such that chamber 24a, 124a is the waste chamber and chamber 24b, 124b is the clean chamber. In this instance, the clean irrigant will be forced out though the opening in the body nose and the used irrigant will be drawn up into the body through the opening in the channel surrounding the nose. These examples are merely illustrative.

The invention claimed is:

1. A combined dental irrigator-vacuum device comprising:
a body having a side wall and a bottom; said side wall defining an opening to said body at a top of said side wall; said body defining a clean chamber and a waste chamber; an outlet in said bottom of said body from said clean chamber and in inlet in said bottom of said body to said waste chamber; said clean chamber outlet and said waste chamber inlet being isolated from each other; and
a pump assembly; said pump assembly comprising;
a base adapted to be received on said body to close said opening of said body; said base comprising a base surface, at least one first opening in said base surface above said clean chamber and at least one second opening in said base surface above said waste chamber;
a valve assembly above said base; said valve assembly comprising a bottom surface, an irrigation valve and a vacuum valve on said valve assembly bottom surface; said irrigation valve and said vacuum valve each comprising a stem extending upwardly from said valve assembly bottom surface, a bottom opening in said valve assembly bottom surface at a bottom of said stem; an upper opening at a top of said stem, a valve seat formed within said stem, and a valve element received within said stem; said valve element being movable between a closed position in which said valve element engages said valve seat to close said valve and an opened position in which said valve element is spaced from said valve seat; said valve element of each said valve being biased to said closed position; and
a compressible cover received on said valve assembly, said compressible cover, at least in part, defining a pump chamber, said irrigation valve and said vacuum valve being positioned within said pump chamber; said cover being movable between a compressed position and a relaxed position; whereby, when said cover is moved to said compressed position; said valve element of said irrigation valve is moved from said closed position to said opened position and when said cover is returned to the relaxed position from the compressed position; the valve element of said vacuum valve is moved from said closed position to said open position.

2. The dental irrigator-vacuum device of claim 1 wherein said valve assembly further includes a peripheral wall extending upwardly from said bottom surface; said cover being mounted to said valve assembly peripheral wall.

3. The dental irrigator-vacuum device of claim 1 wherein said cover is spring biased to said relaxed position.

4. The dental irrigator-vacuum device of claim 1 wherein said pump assembly base further includes a pair of spaced apart walls extending downwardly from said base surface and extending across a bottom of said base surface; said walls defining a slot which is sized and shaped to receive a body divider wall; whereby said base surface cooperates with said body wall and said divider wall to close said clean and waste chambers and to isolate said clean and waste chambers from each other.

5. The dental irrigator-vacuum device of claim 1 wherein said base and said valve assembly are formed as a one-piece integral part; said valve assembly bottom surface being defined by said base surface; and said openings in said base surface defining said bottom openings in said valve stems.

6. The dental irrigator-vacuum device of claim 5 wherein one end of each said stem is closed by a plug; said plug having an opening therein and defining either a top or bottom opening to said valve stems.

7. The dental irrigator-vacuum device of claim 6 wherein one plug is received in the top of said stem of said vacuum valve and a second plug is received in a bottom of said stem of said irrigation valve.

8. The dental irrigator-vacuum device of claim 1 wherein said valve assembly is rotatable between:
(a) an irrigation/vacuum mode in which said irrigation valve is positioned above said clean chamber and said vacuum valve is positioned above said waste chamber and wherein the opening at the bottom of said irrigation valve stem and the opening at the bottom of said vacuum valve stem are aligned with said at least one first opening and said at least one second in said base surface above said clean chamber and said waste chamber, respectively;
(b) an irrigation-only mode wherein said vacuum valve is positioned above said clean chamber with said opening at the bottom of said irrigation valve stem being aligned with an opening in said base above said waste chamber and wherein said vacuum valve is placed in communication with atmosphere; and
(c) a vacuum-only mode wherein said vacuum valve is positioned above said waste chamber with said opening at the bottom of said vacuum valve stem being aligned with said opening in said base surface above said waste chamber and wherein said irrigation valve is placed in communication with atmosphere.

9. The dental irrigator-vacuum device of claim 8 wherein said base comprises a pair of channels on an upper surface of said base; said channels extending inwardly from an edge of said base; said channels being positioned such that when said device is in said irrigation-only mode said vacuum valve is positioned above a first of said pair of channels and when said device is in said vacuum-only mode said irrigation valve is positioned above a second of said pair of channels.

10. The dental irrigator-vacuum device of claim 8 wherein said base comprises an upwardly extending post and said valve assembly includes an opening in said bottom surface through which said base post extends; said valve assembly being rotatable about said base post and said base post defining an axis of rotation for said valve assembly.

11. The irrigator-vacuum device of claim 10 wherein said valve assembly comprises a tube extending upwardly from said opening in said valve assembly bottom surface; said pump assembly base being received in said valve assembly tube.

12. The irrigator-vacuum device of claim 1 comprising a nose at a bottom of said body and a collar surrounding said nose; said nose and said collar, in combination, defining an annular channel; said nose including a passage therethrough in communication with one of the clean chamber outlet and waste chamber inlet; and the other of said clean chamber outlet and waste chamber inlet being in opening into said annular channel.

13. A combined dental irrigator-vacuum device comprising:
a device body having a side wall and a bottom defining a volume; a divider wall within said body and dividing said volume into a clean chamber and a waste chamber; an outlet in said body bottom from said clean chamber and in inlet in said body bottom to said waste chamber; said clean chamber outlet and said waste chamber inlet being isolated from each other; and
a pump assembly comprising;
a base member adapted to be received on a top of said device body and comprising a base surface, at least one first opening in said base surface above said clean chamber, at least one second opening in said base surface above said waste chamber, and a pair of channels extending inwardly from a peripheral edge of said base member;
a valve assembly above said base member; said valve assembly being rotatable relative to said base member and comprising a bottom surface, an irrigation valve and a vacuum valve on said valve assembly bottom surface; said irrigation valve and said vacuum valve each comprising a stem extending upwardly from said valve assembly bottom surface, a bottom opening in said valve assembly bottom surface at a bottom of said stem; an upper opening at a top of said stem, a valve seat formed within said stem, and a valve element received within said stem; said valve element being movable between a closed position in which said valve element engages said valve seat to close said valve and an opened position in which said valve element is spaced from said valve seat; said valve element of each said valve being biased to said closed position; said valve assembly being selectively switchable between:
(a) an irrigation/vacuum mode in which said irrigation valve is positioned above said clean chamber and said vacuum valve is positioned above said waste chamber and wherein the opening at the bottom of said irrigation valve stem and the opening at the bottom of said vacuum valve stem are aligned with said at least one first opening and said at least one second in said base surface above said clean chamber and said waste chamber, respectively;
(b) an irrigation-only mode wherein said irrigation valve is positioned above said clean chamber with said opening at the bottom of said irrigation valve stem aligned with said at least one first opening in said base surface above said clean chamber and wherein said vacuum valve is above a first channel of said pair of channels; and
(c) a vacuum-only mode wherein said vacuum valve is positioned above said waste chamber with said opening at the bottom of said vacuum valve stem being aligned with said at least one second opening in said base surface above said waste chamber; and wherein said irrigation valve is positioned above a second of said pair of channels.

14. The dental irrigator-vacuum device of claim 13 further comprising a seal member positioned between said base member and said valve assembly; said seal member comprising holes aligned with said at least one first opening, said at least one second opening, and said channels of said base member; said seal member defining a seal between said valve assembly bottom openings and said base openings and channels.

15. The dental irrigator-vacuum device of claim 13 further comprising a compressible cover received on said valve assembly and defining a pump chamber, said valves being positioned within said pump chamber; said cover being movable between a compressed position and a relaxed position; whereby, when said cover is moved to said compressed position; said valve element of said irrigation valve is moved from said closed position to said opened position and when said cover is returned to the relaxed position from the compressed position; the valve element of said vacuum valve is moved from said closed position to said open position.

16. The dental irrigator-vacuum device of claim 15 wherein said valve assembly further includes a peripheral wall extending upwardly from said bottom surface; said cover being mounted to said valve assembly peripheral wall.

17. The dental irrigator-vacuum device of claim 15 wherein said cover is spring biased to said relaxed position.

18. The dental irrigator-vacuum device of claim 13 wherein said pump assembly base member further includes a pair of spaced apart walls extending downwardly from said base surface and extending across said base surface; said walls defining a slot which is sized and shaped to receive said body divider wall; whereby said base surface cooperates with said body wall and said divider wall to close said clean and waste chambers and to isolate said clean and waste chambers from each other.

19. The irrigator-vacuum device of claim 13 wherein said base member comprises an upwardly extending post and said valve assembly includes an opening in said bottom surface through which said base member post extends; said valve assembly being rotatable about said base member post and said base member post defining an axis of rotation for said valve assembly.

20. The irrigator-vacuum device of claim 19 wherein said valve assembly comprises a tube extending upwardly from said opening in said valve assembly bottom surface; said pump assembly base post being received in said valve assembly tube.

21. The dental irrigator-vacuum device of claim 13 comprising indicia on said base assembly and said valve assembly; wherein said indicia on said base member is indicative of a position to which said valve assembly is to be rotated to place said device in said modes of operation.

* * * * *